United States Patent
Hashimoto et al.

(10) Patent No.: US 10,806,534 B2
(45) Date of Patent: Oct. 20, 2020

(54) INFORMATION SHARING SYSTEM AND METHOD OF SHARING INFORMATION BETWEEN A PLURALITY OF ROBOT SYSTEMS

(71) Applicant: KAWASAKI JUKOGYO KABUSHIKI KAISHA, Kobe-shi, Hyogo (JP)

(72) Inventors: Yasuhiko Hashimoto, Kobe (JP); Masayuki Kamon, Akashi (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 260 days.

(21) Appl. No.: 15/755,139

(22) PCT Filed: May 27, 2016

(86) PCT No.: PCT/JP2016/002585
§ 371 (c)(1),
(2) Date: Feb. 26, 2018

(87) PCT Pub. No.: WO2017/033358
PCT Pub. Date: Mar. 2, 2017

(65) Prior Publication Data
US 2018/0243916 A1 Aug. 30, 2018

(30) Foreign Application Priority Data
Aug. 25, 2015 (JP) .................................. 2015-165479

(51) Int. Cl.
*G05B 19/418* (2006.01)
*A61B 34/37* (2016.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC ......... A61B 34/32; A61B 34/37; B23P 19/04; B23P 21/00; B23P 21/002; B23Q 15/12;
(Continued)

(56) References Cited

U.S. PATENT DOCUMENTS 5,136,223 A 8/1992 Karakama et al.
6,645,196 B1 * 11/2003 Nixon ................... B25J 9/1664
128/898

(Continued)

FOREIGN PATENT DOCUMENTS

JP H02-160487 A 6/1990
JP H10-44074 A 2/1998
(Continued)

OTHER PUBLICATIONS

Aug. 2, 2016 International Search Report issued in International Patent Application No. PCT/JP2016/002585.

*Primary Examiner* — Harry Y Oh
(74) *Attorney, Agent, or Firm* — Oliff PLC

(57) ABSTRACT

An information sharing system between a plurality of robot systems includes a plurality of robot systems, communicatably connected with each other through a network, and configured to be capable of presetting a given operation of a robot and repeating a correction of the operation, and a storage device, connected with the network and configured to store corrected information containing corrected operating information that is operating information for causing the robot to execute a given operation corrected in at least one of the robot systems. Each of the plurality of robot systems (Continued)

shares the corrected information stored in the storage device and operates the robot based on the sharing corrected information.

6 Claims, 11 Drawing Sheets

(51) Int. Cl.

| | |
|---|---|
| *B25J 9/00* | (2006.01) |
| *B23P 19/04* | (2006.01) |
| *B25J 13/00* | (2006.01) |
| *B25J 19/04* | (2006.01) |
| *B25J 9/16* | (2006.01) |
| *B25J 13/08* | (2006.01) |
| *B25J 3/00* | (2006.01) |
| *B25J 13/06* | (2006.01) |
| *B25J 18/00* | (2006.01) |
| *B25J 19/02* | (2006.01) |
| *B25J 3/04* | (2006.01) |
| *B23Q 15/12* | (2006.01) |
| *B25J 13/02* | (2006.01) |
| *B25J 11/00* | (2006.01) |
| *G06F 3/01* | (2006.01) |
| *H04N 5/232* | (2006.01) |
| *H04N 7/18* | (2006.01) |
| *A61B 34/32* | (2016.01) |
| *G06T 7/62* | (2017.01) |
| *G06T 7/70* | (2017.01) |
| *B23P 21/00* | (2006.01) |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC ........ B25J 11/008; B25J 13/00; B25J 13/003; B25J 13/006; B25J 13/02; B25J 13/025; B25J 13/06; B25J 13/065; B25J 13/08; B25J 13/084; B25J 13/085; B25J 13/087; B25J 13/088; B25J 18/00; B25J 19/023; B25J 19/028; B25J 19/04; B25J 3/00; B25J 3/04; B25J 9/0081; B25J 9/0084; B25J 9/0087; B25J 9/1602; B25J 9/161; B25J 9/1612; B25J 9/1628; B25J 9/163; B25J 9/1633; B25J 9/1646; B25J 9/1653; B25J 9/1664; B25J 9/1669; B25J 9/1674; B25J 9/1682; B25J 9/1689; B25J 9/1697; G05B 19/4182; G05B 2219/33007; G05B 2219/35464; G05B 2219/37297; G05B 2219/39004; G05B 2219/39102; G05B 2219/39439; G05B 2219/39531; G05B 2219/39533; G05B 2219/40022; G05B 2219/40134; G05B 2219/40136; G05B 2219/40139; G05B 2219/40142; G05B 2219/40143; G05B 2219/40145; G05B 2219/40146; G05B 2219/40161; G05B 2219/40162; G05B 2219/40163; G05B 2219/40169; G05B 2219/40182; G05B 2219/40183; G05B 2219/40195; G05B 2219/40387; G05B 2219/40627; G06F 3/017; G06T 7/62; G06T 7/70; H04N 5/23219; H04N 7/181; Y10S 901/02; Y10S 901/03; Y10S 901/08; Y10S 901/09; Y10S 901/10; Y10S 901/27; Y10S 901/41; Y10S 901/46; Y10S 901/47
See application file for complete search history.

(56) References Cited

U.S. PATENT DOCUMENTS

| | | | |
|---|---|---|---|
| 2010/0152899 A1* | 6/2010 | Chang | B25J 9/1682 700/262 |
| 2010/0268386 A1* | 10/2010 | Kiyota | G05B 19/42 700/264 |
| 2010/0325623 A1* | 12/2010 | Ikeda | G06F 8/65 717/173 |
| 2011/0301733 A1* | 12/2011 | Yoshima | B23K 9/0216 700/96 |
| 2012/0191245 A1* | 7/2012 | Fudaba | B25J 9/1633 700/254 |
| 2014/0121834 A1* | 5/2014 | Ogawa | A61B 34/30 700/257 |
| 2014/0160015 A1* | 6/2014 | Ogawa | B25J 13/02 345/156 |

(56) References Cited

U.S. PATENT DOCUMENTS

2015/0352720 A1* 12/2015 Iizuka .................... B25J 9/1664
                                                                                            700/245
2017/0249435 A1* 8/2017 Lancelot ................ G06Q 50/24

FOREIGN PATENT DOCUMENTS

| JP | 2003-311661 A | 11/2003 |
| JP | 2009-262279 A | 11/2009 |
| JP | 2013-071231 A | 4/2013 |

* cited by examiner

| CORRECTED OPERATING INFO | NUMBER OF CORRECTIONS (N) | WEIGHTING VALUE (W) |
|---|---|---|
| FACTORY A | $L_{100}$ | 50 | 0.1 |
| FACTORY B | $L_{1000}$ | 1000 | 0.7 |
| ... | ... | ... | ... |
| FACTORY E | $L_{500}$ | 500 | 0.3 |

FIG. 8

INFORMATION SHARING SYSTEM AND METHOD OF SHARING INFORMATION BETWEEN A PLURALITY OF ROBOT SYSTEMS

TECHNICAL FIELD

The present disclosure relates to an information sharing system and a method of sharing information between a plurality of robots.

BACKGROUND ART

Conventionally, at manufacturing sites, a repeat work, such as welding, painting, assembling of components, application of seal adhesive, is automatically performed by an industrial robot. In order to make the robot perform the work, it is necessary to instruct the robot with information required for the work to store the information in the robot. The instructing method of the robot includes, for example, direct teaching in which a teacher directly touches the robot to move it, teaching by a remote control using a teaching pendant, teaching by programming, and teaching by a master and a slave. For example, Patent Document 1 discloses one example of the teaching work to make a robot arm store a route of a work by the direct teaching.

Meanwhile, it may be necessary to partially change the operation taught to the robot due to various reasons. For example, if a work object, a work environment etc. of the robot has partially changed from the taught one, problems of becoming impossible for the robot to carry out the target work, and degrading an accuracy of the work, may arise. Moreover, after the teaching work has finished, it may be found in the initially-created teaching information that there is a fault in part of the work. In such a case, the teaching work is again performed to change the teaching information to be used for an automatic operation of the robot.

REFERENCE DOCUMENT OF CONVENTIONAL ART

Patent Document

[Patent Document 1] JP2013-071231A

DESCRIPTION OF THE DISCLOSURE

Problems to be Solved by the Disclosure

However, skilled person's techniques are needed for the teaching in many cases, and this requires a large amount of time and labors, resulting in the teacher's burden. This is similar for the case where the part of the robot operation is changed. In recent years, Japan has faced a problem of a decrease in the absolute number of skilled persons, in connection with the decreases in birthrate and the aging of population. Especially, this problem is more serious at manufacturing sites where many industrial robots are introduced.

Therefore, one purpose of the present disclosure is to effectively utilize skilled person's techniques at a manufacturing site where many industrial robots are introduced.

SUMMARY OF THE DISCLOSURE

An information sharing system between a plurality of robot systems according to one aspect of the present disclosure, includes a plurality of robot systems, communicatably connected with each other through a network, and configured to be capable of presetting a given operation of a robot and repeating a correction of the operation, and a storage device, connected with the network and configured to store corrected information containing corrected operating information that is operating information for causing the robot to execute a given operation corrected in at least one of the robot systems. Each of the plurality of robot systems shares the corrected information stored in the storage device and operates the robot based on the sharing corrected information.

According to this configuration, the corrected information for the robot corrected by one skilled person in the one robot system is shared in each of the plurality of robot systems. The robot can be operated based on the sharing corrected information. Therefore, burdens of the correction in other robot systems and setup of a new robot system are reduced.

The plurality of robot systems may be installed in each of a plurality of factories, acquire the corrected information of the plurality of robot systems from each of the plurality of factories, and add to the corrected operating information contained in the acquired corrected information, weighting values according to the number of corrections, to determine optimal operation of the robot.

According to this configuration, since the weighting value according to the number of corrections is added to the corrected operating information of the plurality of robot systems acquired from each of the plurality of factories, the reliability of sample data improves. Thus, the optimal operation of the robot can be determined and all the factories can share the information. As a result, the burdens of the correction of the robot systems in each factory and the setup of a new robot system at the time of a factory construction are reduced.

The plurality of robot systems may be installed in each of a plurality of factories, acquire the corrected information of the plurality of robot systems from each of the plurality of factories, and add to the corrected operating information contained in the acquired corrected information, the weighting values according to a latest correction amount among correction amounts that are differences between a previous value and a present value of the corrected operating information, to determine optimal operation of the robot.

According to this configuration, since the weighting value according to magnitude of the latest correction amount among the correction amounts that are the differences between the previous value and the present value of the corrected operating information, is added to the corrected operating information of the plurality of robot systems acquired from each of the plurality of factories, the reliability of sample data further improves. Thus, the optimal operation of the robot can be determined and all the factories can share the information.

The plurality of robot systems may be installed in each of a plurality of factories where work environments differ from each other. The system may further include a situation information acquisition part configured to acquire situation information indicative of a situation of each of the plurality of factories. The system may acquire the corrected information and the situation information of the plurality of robot systems from each of the plurality of factories, and add to the corrected operating information contained in the acquired corrected information, the weighting values according to the situation information, to determine the optimal operation of the robot for each of the plurality of factories.

According to this configuration, since the weighting value according to the situation information of each factory is added to the acquired corrected operating information, the optimal operation of the robot can be determined for each of the plurality of factories, and all the factories can share the information. Thus, a difference of work environments between the factories is absorbed, and the burdens of the correction of the robot system in each factory and the setup of a new robot system at the time of the factory construction are reduced. Moreover, the weighting value may be added to the sharing information according to the work environment for each factory.

In the robot system described above, a robot main body may be a slave arm, and an operation correcting device may be a master arm installed outside a work area of the slave arm.

A method of sharing information according to another aspect of the present disclosure is a method of sharing information between a plurality of robot systems, the plurality of robot systems communicatably connected with each other through a network, and configured to preset a given operation of a robot and repeat a correction of the operation. The method includes storing in a storage device connected with the network, corrected information containing corrected operating information that is operating information for causing the robot to execute a given operation corrected in at least one of the robot systems, sharing the corrected information stored in the storage device, in each of the plurality of robot systems, and operating the robot based on the sharing corrected information.

Effect of the Disclosure

According to the present disclosure, the skilled person's techniques are effectively utilized at the manufacturing sites where many industrial robots are introduced.

The purpose described above, other purposes, features, and advantages of the present disclosure will be made clear from the following detailed description of suitable embodiments with reference to the accompanying drawings.

BRIEF DESCRIPTION OF DRAWINGS

FIG. 8 is one example of data managed by the server of FIG. 1.

MODES FOR CARRYING OUT THE DISCLOSURE

Figure 1:
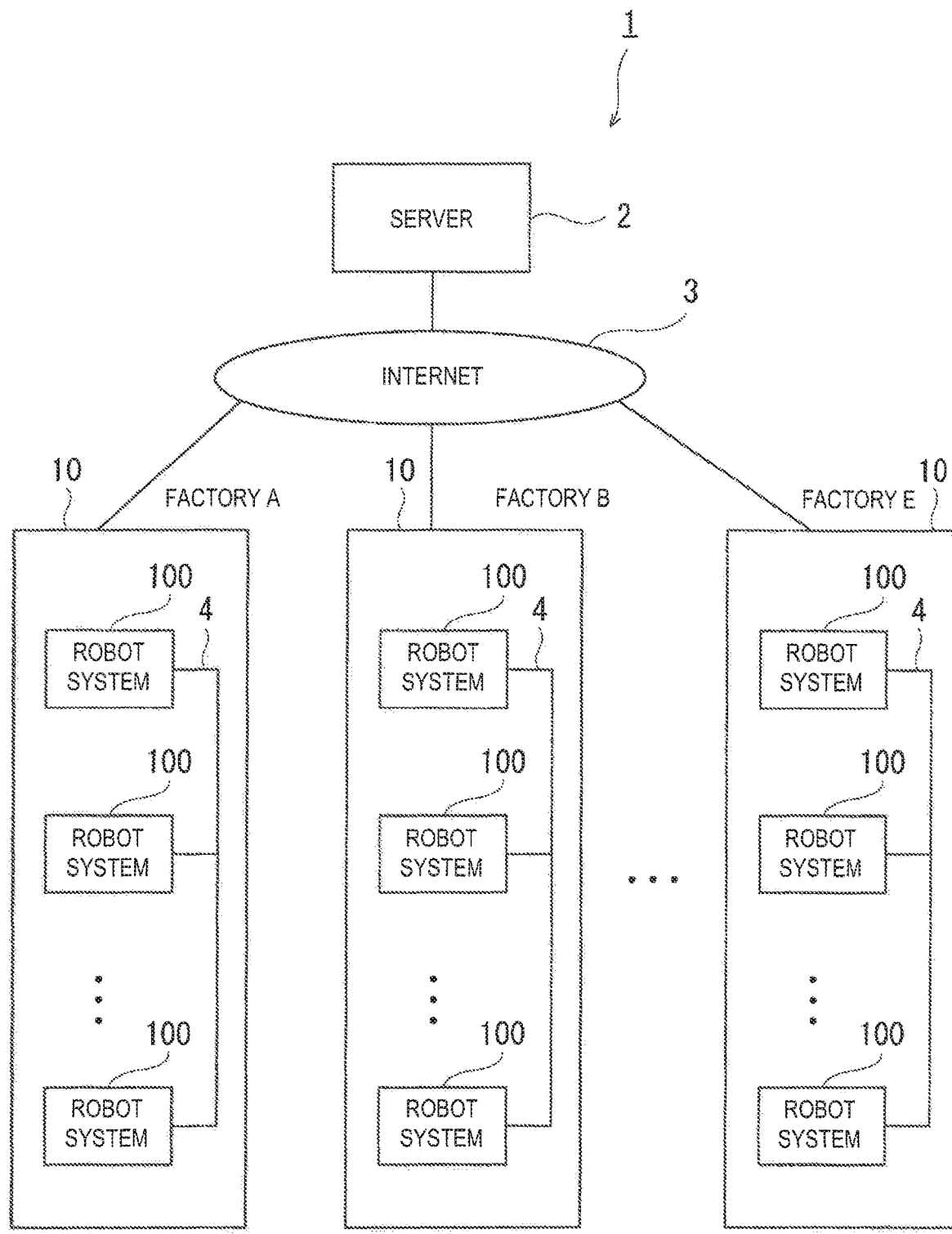
FIG. 1 is a schematic view illustrating a configuration of an information sharing system between a plurality of robots according to a first embodiment.

Hereinafter, embodiments according to the present disclosure will be described with reference to the drawings. Below, the same reference characters are given to the same or corresponding components throughout the drawings to omit redundant description.

First Embodiment

[Information Sharing System]

FIG. 1 is a schematic view illustrating a configuration of an information sharing system 1 between a plurality of robots according to a first embodiment. As illustrated in FIG. 1, the information sharing system 1 includes a plurality of factories 10 connected to the Internet 3, and a server 2 connected with the plurality of factories 10 through the Internet 3. In this information sharing system 1, the plurality of factories 10 are capable of sharing information stored in the server 2 through the Internet 3.

The server 2 is, for example, an information processing device, such as a personal computer, provided with a CPU (Central Processing Unit), a storage device, and a communication interface. Although the server 2 is installed independently from the plurality of factories 10 in this embodiment, it may be installed in a mother factory, or may be installed in any of the plurality of factories 10.

Each of the plurality of factories 10 is located in different environment. Each of the plurality of factories 10 is located in a different country. In FIG. 1, the factories A to E are illustrated, and, for example, the factory A is located in the U.S., the factory B in Russia, and the factory E in China. A plurality of robot systems 100 are installed in each of the plurality of factories 10. The plurality of robot systems 100 of each factory 10 are communicatably connected with each other through LAN 4 (Local Area Network). The plurality of robot systems 100 are capable of sharing information stored in each of the robot systems 100 through the LAN 4.

The robot system 100 of this embodiment is a system utilizing a master-slave type robot. In the robot system 100, at each factory 10, an operator who is located at a position distant from a work area of a slave arm 101 (outside of the work area) is able to move a master arm 102 to input instructions so that the slave arm 101 performs operation corresponding to the instructions to perform a specific work (see FIG. 2). Moreover, in the robot system 100, the slave arm 101 is also capable of automatically performing a specific work, without the manipulation of the master arm 102 by the operator. In this embodiment, each of the plurality of robot systems 100 repeats a specific work (e.g., welding, painting, and assembling of component(s)) which is common to each factory 10 to manufacture the same products. An operating mode in which the slave arm 101 is operated according to the instructions inputted through the master arm 102 is herein referred to as a "manual mode." Note that the "manual mode" also includes a case where part of the operation of the slave arm 101 under operation is automatically corrected based on the instructions inputted by the operator manipulating the master arm 102. Moreover, an operating mode in which the slave arm 101 is operated according to a preset task program is referred to as an "automatic mode."

Further, the robot system 100 of this embodiment is configured so that the operation to be carried out automatically is correctable, while the slave arm 101 is operating automatically, by reflecting the manipulation of the master arm 102 on the automatic operation of the slave arm 101. That is, the robot system 100 is configured so that a given operation of the slave arm 101 is able to be preset, and the operation is repeatedly correctable. The robot system 100 includes a storage device 106 (see FIG. 2) which stores corrected information containing corrected operating information which is operating information for causing the robot to perform corrected given operation. An operating mode in which the slave arm 101 is operated according to the preset task program in a state where the instructions inputted through the master arm 102 is reflectable is herein referred to as a "correctable automatic mode." Note that the "automatic mode" described above is distinguished from the "correctable automatic mode" in that the manipulation of the master arm 102 is not reflected in the operation of the slave arm 101 when the operating mode in which the slave arm 101 is operated is the automatic mode.

[Configuration of Robot System]

Figure 2:
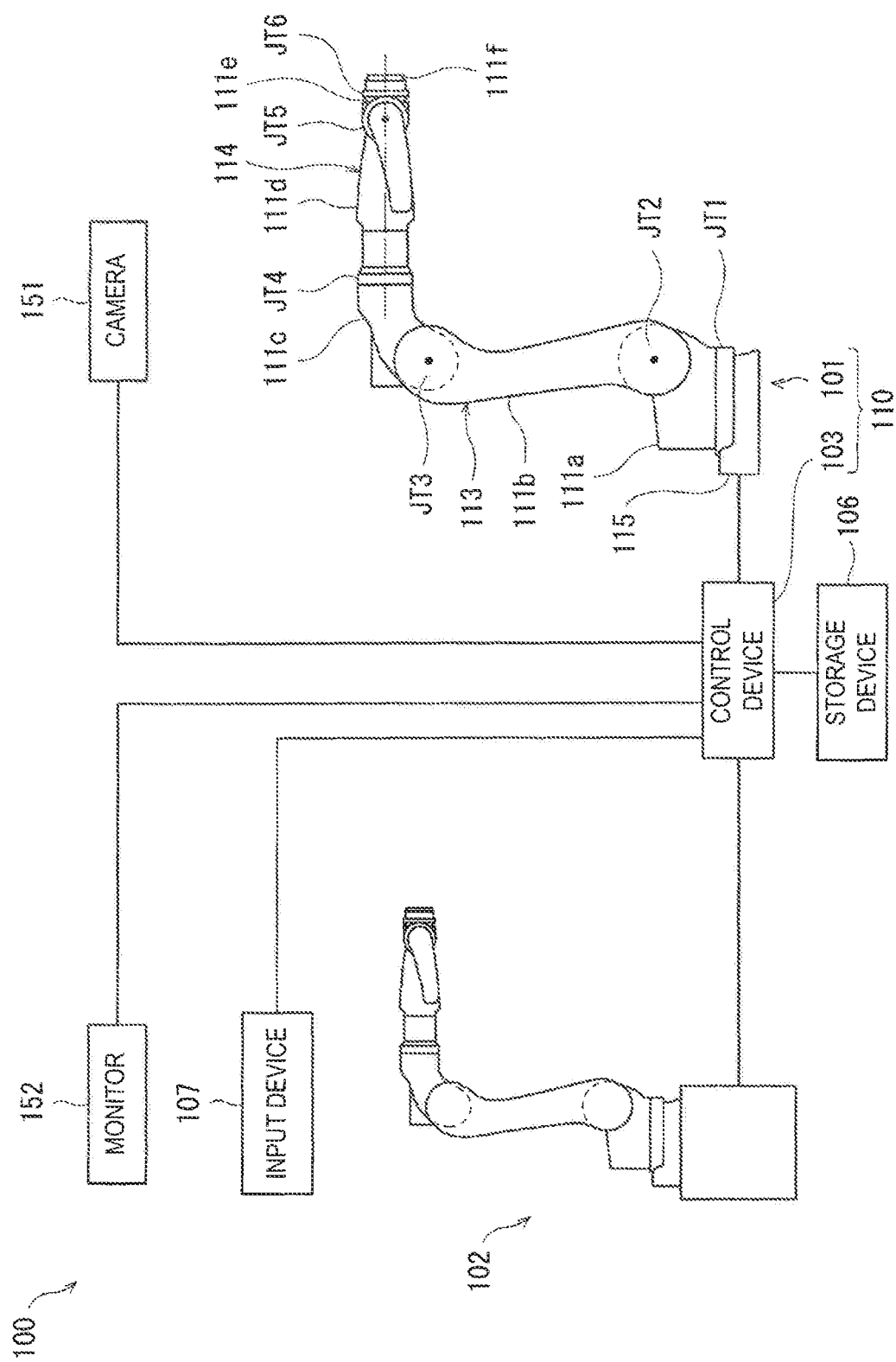
FIG. 2 is a schematic diagram illustrating a configuration of a robot system of FIG. 1.

FIG. 2 is a schematic diagram illustrating one example of a configuration of the robot system 100. As illustrated in FIG. 2, the robot system 100 includes a slave robot 110, the master arm 102, a camera 151, a monitor 152, the storage device 106, and an input device 107.

The slave robot 110 includes the slave arm 101, an end effector (not illustrated) attached to a tip end of the slave arm 101, and a control device 103 which governs operations of the slave arm 101 and the end effector. The slave arm 101 includes a pedestal 115, an arm part 113 supported by the pedestal 115, and a wrist part 114 which is supported by a tip end of the arm part 113 and to which an end effector is attached.

As illustrated in FIG. 2, the slave arm 101 is an articulated robot arm having a plurality of (three or more) joints JT1-JT6, which is constructed by serially coupling a plurality of links 111a-111f. In more detail, at the first joint JT1, the pedestal 115 and a base-end part of the first link 111a are coupled to each other so as to be rotatable about an axis extending vertically. At the second joint JT2, a tip-end part of the first link 111a and a base-end part of the second link 111b are coupled to each other so as to be rotatable about an axis extending horizontally. At the third joint JT3, a tip-end part of the second link 111b and a base-end part of the third link 111c are coupled to each other so as to be rotatable about an axis extending horizontally. At the fourth joint JT4, a tip-end part of the third link 111c and a base-end part of the fourth link 111d are coupled to each other so as to be rotatable about an axis extending in the longitudinal directions of the fourth link 111c. At the fifth joint JT5, a tip-end part of the fourth link 111d and a base-end part of the fifth link 111e are coupled to each other so as to be rotatable about an axis perpendicular to the longitudinal directions of the link 111d. At the sixth joint JT6, a tip-end part of the fifth link 111e and a base-end part of the sixth link 111f are twistably and rotatably coupled to each other. A mechanical interface is provided to a tip-end part of the sixth link 111f. The end effector corresponding to the contents of work is attached to the mechanical interface attachably and detachably.

The arm part 113 of the slave arm 101 is formed by a coupled body of the links and the joints, which is comprised of the first joint JT1, the first link 111a, the second joint JT2, the second link 111b, the third joint JT3, and the third link 111c, described above. Moreover, the wrist part 114 of the slave arm 101 is formed by a coupled body of the links and the joints, which is comprised of the fourth joint JT4, the fourth link 111d, the fifth joint JT5, the fifth link 111e, the sixth joint JT6, and the fourth link 111f, described above.

The joints JT1-JT6 are provided with drive motors M1-M6, respectively, each of which is one example of an actuator which relatively rotates two members connected by the joint. The drive motors M1-M6 are, for example, servo motors which are servo-controlled by the control device 103. Moreover, the joints JT1-JT6 are provided with rotation sensors E1-E6 (see FIG. 3) which detect rotational positions of the drive motors M1-M6, and current sensors C1-C6 (see FIG. 3) which detect current for controlling the rotations of the drive motors M1-M6, respectively. The rotation sensors E1-E6 are, for example, encoders. Note that, in the description of the drive motors M1-M6, the rotation sensors E1-E6, and the current sensors C1-C6, 1-6 of suffixes are given to the alphabet corresponding to the joints JT1-JT6, respectively. Below, when an arbitrary joint is illustrated among the joints JT1-JT6, the suffix is omitted and it is referred to as "JT," and the same is applied to the drive motor M, the rotation sensor E, and the current sensor C.

The control device 103 may be comprised of, for example, an arithmetic part (not illustrated), such as a microcontroller, an MPU, a PLC (Programmable Logic Controller), a logic circuit, etc., and a memory part (not illustrated), such as a ROM, a RAM, etc.

Figure 3:
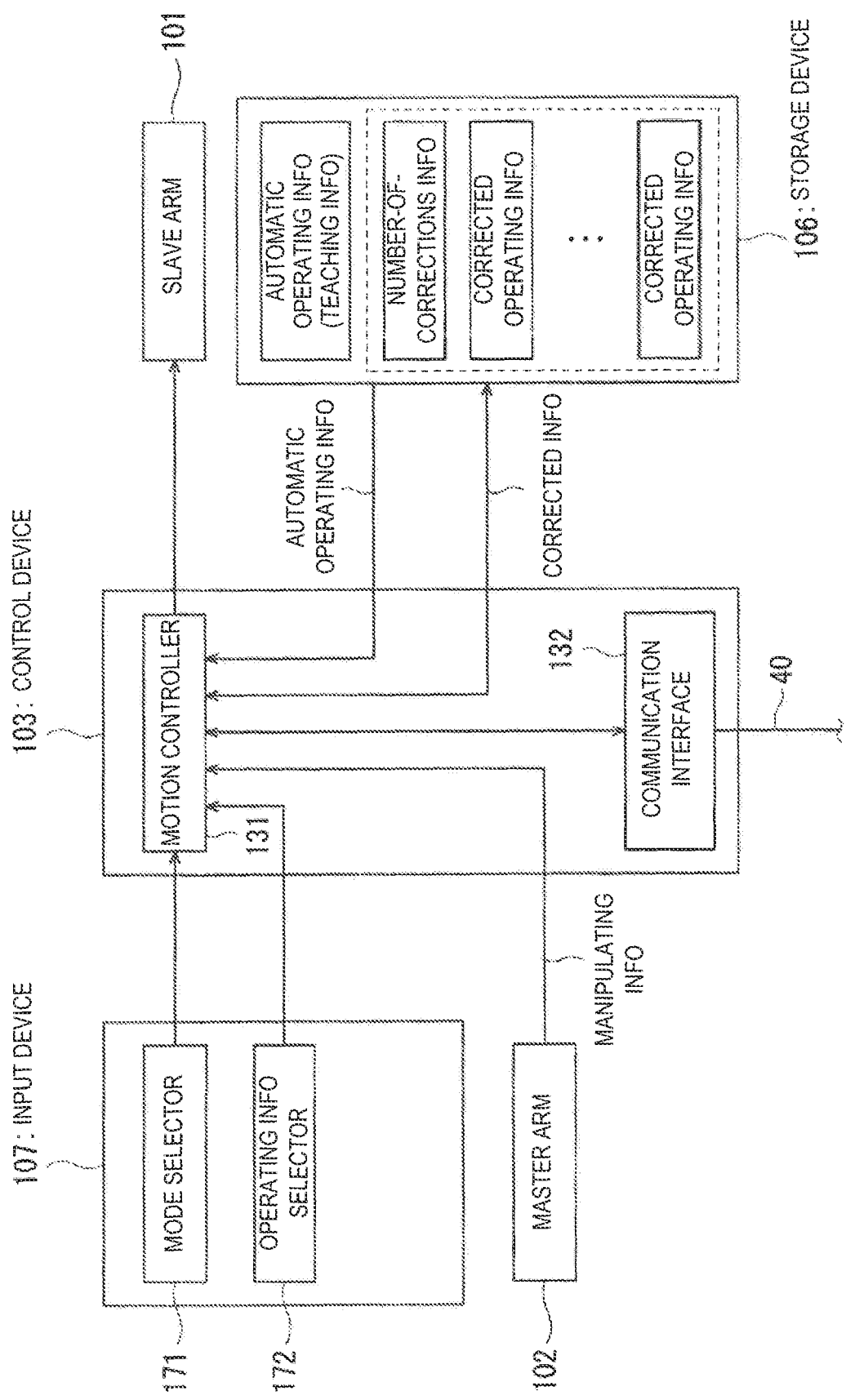
FIG. 3 is a schematic diagram illustrating a configuration of a control system of the robot system of FIG. 2.

FIG. 3 is a schematic diagram illustrating a configuration of a control system of the robot system 100. As illustrated in FIG. 3, the control device 103 includes a motion controller 131 and a communication interface 132, as functional blocks. The motion controller 131 controls the operation of the slave arm 101. The control of the operation of the slave arm 101 by the motion controller 131 will be described later in detail. The functional blocks provided to the control device 103 may be implemented by, for example, the arithmetic part of the control device 103 reading and executing the program stored in the memory part. The communication interface 132 is connected with a router (not illustrated) through a LAN cable 40. The plurality of robot systems 100 are connected with each other through the LAN cable 40 and the router. Thus, each robot system 100 of the plurality of robot systems 100 is capable of sharing the corrected information stored in the storage device 106 through LAN 3.

The master arm 102 is a device which is installed outside the work area of the slave arm 101 and receives manipulating instructions from the operator. Since the master arm 102 has a similarity structure to that of the slave arm 101, description related to the configuration of the master arm 102 is omitted. Note that the master arm 102 may have a non-similarity structure to that of the slave arm 101. By moving the master arm 102, the manipulating information is generated, and the generated manipulating information is sent to the control device 103. In the robot system 100 of this embodiment, when the operating mode in which the slave arm 101 is operated is the manual mode, the slave arm 101 is controlled by the control device 103 so that it moves to follow the motion of the master arm 102 in response to the manipulating information being sent to the control device 103. When the operating mode in which the slave arm 101 is operated is the correctable automatic mode, the operation of the slave arm 101 which is operating automatically is corrected by using the manipulating information in response to the manipulating information being sent to the control device 103. As will be described later, in this embodiment, the master arm 102 functions as an operation correcting device which corrects the operation of the slave arm 101 during operation.

Returning to FIG. 2, the camera 151 is a camera which images a work situation of the slave arm 101, and the monitor 152 is a monitor for the operator to check the work situation of the slave arm 101. The camera 151 is installed in a space where the slave arm 101 is provided, and the monitor 152 is installed in a space where the master arm 102 is provided. The operator manipulates the master arm 102, while looking at the work situation of the slave arm 101 displayed on the monitor 152. The camera 151 and the monitor 152 are connected with each other through the control device 103, and imaging information imaged by the camera 151 is sent to the monitor 152 through the control device 103. Note that the camera 151 and the monitor 152 may be directly connected to each other, without the intervention of the control device 103. The camera 151 and the monitor 152 may be connected wiredly or wirelessly.

The input device 107 is an input device which is installed outside the work area together with the master arm 102, receives the manipulating instructions from the operator, and inputs the received manipulating instructions into the control device 103. The input device 107 is operably configured, and may include, for example, a switch, an adjustment knob, a control lever, or a mobile terminal, such as a tablet computer.

As illustrated in FIG. 3, the input device 107 includes a mode selector 171 and an operating information selector 172. The mode selector 171 is for the operator to select the operating mode in which the slave arm 101 is operated from the automatic mode, the correctable automatic mode, and the manual mode, described above. The operating information selector 172 is to select from a plurality of operating information for causing the slave arm 101 to operate, operating information to be used by the motion controller 131 when the slave arm 101 is operated in the automatic mode or the correctable automatic mode.

The storage device 106 is a readable and writable recording medium, and stores automatic operating information for causing the slave arm 101 to automatically carry out a given operation. The automatic operating information needs not to be all the information required for causing the slave arm 101 to automatically carry out the given operation, but may be some of the information. Moreover, the automatic operating information may be any kind of information as long as it is information related to the operation of the slave arm 101. For example, the automatic operating information may be route information containing time-series data, or may be path information which represents a pause of discontinuous points. The automatic operating information may contain, for example, a speed along the route of the slave arm 101. In this embodiment, the automatic operating information is, for example, teaching information which is stored by a teaching work in which the slave arm 101 is operated to perform a given work. In this embodiment, although the automatic operating information as the teaching information is information which is stored by instructing the operation of the slave arm 101 by manipulating the master arm 102, it is not limited to this configuration, but may be information stored by any kind of teaching method. For example, the automatic operating information as the teaching information may be information stored by the direct teaching.

The storage device 106 is configured to automatically store the corrected information (illustrated by a dashed line) containing the corrected operating information for causing the slave arm 101 to perform the corrected operation when the slave arm 101 performs the corrected operation. Here, the corrected information is configured so that the corrected operating information and its number-of-corrections information are automatically stored. Moreover, the corrected operating information may be any kind of information as long as it is information for causing the slave arm 101 to perform the corrected operation. For example, the corrected operating information may be route information containing time-series data, or may be the path information illustrating a pause of discontinuous points. Note that, in the robot system 100 according to this embodiment, although the storage device 106 is provided separately from the control device 103, it may be provided integrally with the control device 103.

Below, the control of the operation of the slave arm 101 by the motion controller 131 is described with reference to FIG. 3.

The motion controller 131 reads from the storage device 106 the automatic operating information for causing the slave arm 101 to operate automatically. Moreover, the manipulating information which is generated by manipulating the master arm 102 is inputted into the motion controller 131 from the input device 107.

The motion controller 131 uses one or both of the automatic operating information and the manipulating information according to the operating mode selected in the mode selector 171.

When the operating mode selected in the mode selector 171 is the manual mode, the motion controller 131 uses the manipulating information.

In more detail, when the operating mode in which the slave arm 101 is operated is the manual mode, the motion controller 131 controls the operation of the slave arm 101 according to the manipulating information (input instructions) sent by manipulating the master arm 102, without using the automatic operating information (teaching information) stored in the storage device 106.

Moreover, when the operating mode selected in the mode selector 171 is the automatic mode, the motion controller 131 uses the automatic operating information (teaching information). In more detail, when the operating mode in which the slave arm 101 is operated is the automatic mode, the motion controller 131 controls the operation of the slave arm 101 by using the automatic operating information (teaching information) sent from the storage device 106 according to the preset task program, without using the manipulating information sent from the master arm 102.

Moreover, when the operating mode selected in the mode selector 171 is the correctable automatic mode, the motion controller 131 generates the corrected operating information by using the automatic operating information (teaching information) and the manipulating information. Note that, while the operating mode is the correctable automatic mode, the motion controller 131 uses only the automatic operating information (teaching information) if the manipulating information has not been sent to the motion controller 131. In more detail, while the operating mode in which the slave arm 101 is operated is the correctable automatic mode, the motion controller 131 generates the corrected operating information by using the automatic operating information (teaching information) and the manipulating information in response to the manipulating information being received when the slave arm 101 is operating automatically using the automatic operating information, and controls the operation of the slave arm 101 by using the corrected operating information. Thus, the slave arm 101 performs operation corrected from the operation related to the automatic operating information, i.e., the operation to be performed automatically.

Figure 4:
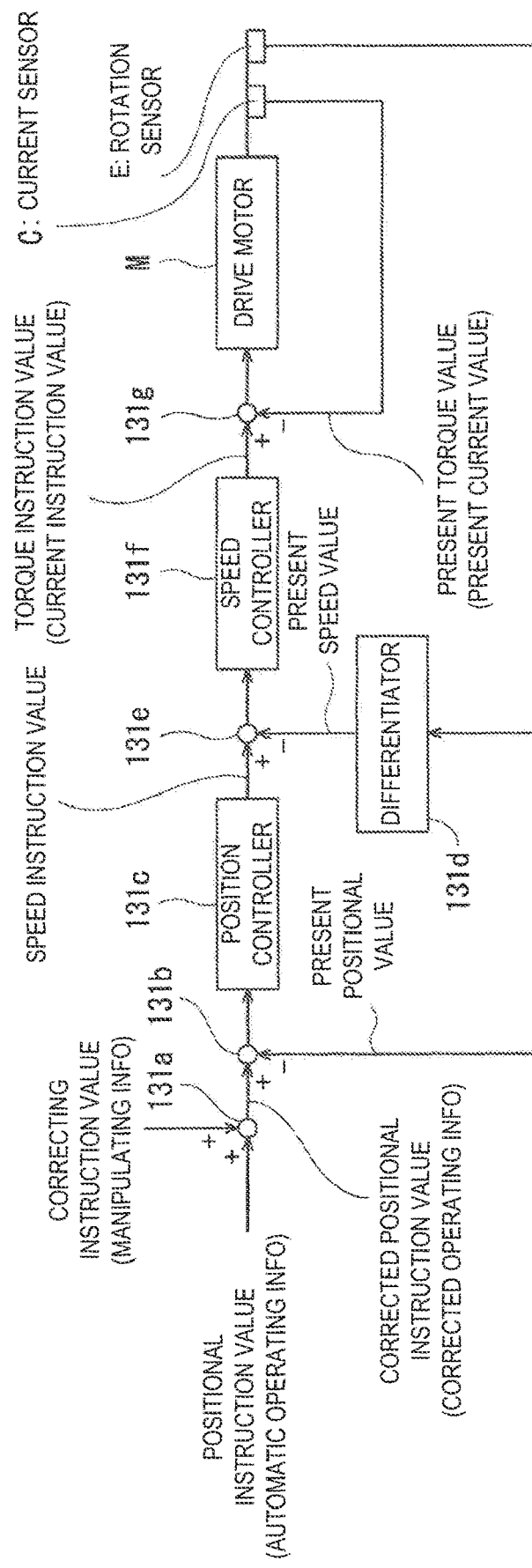
FIG. 4 is a view illustrating one example of a block diagram of a control system of a motion controller of FIG. 3.

Below, the operational correction of the slave arm 101 when the operating mode in which the slave arm 101 is operated is the correctable automatic mode is described with reference to FIG. 4. FIG. 4 is a view illustrating one example of a block diagram of a control system of the motion controller 131. In this example, the automatic operating information and the manipulating information are, for example, the route information containing the time-series data.

The motion controller 131 includes an adder 131a, subtractors 131b, 131e and 131g, a position controller 131c, a differentiator 131d, and a speed controller 131f, and controls the rotational position of the drive motor M of the slave arm 101 according to an instruction value based on the automatic operating information, and an instruction value based on the manipulating information.

The adder 131a generates a corrected positional instruction value (corrected operating information) by adding a corrected instruction value based on the manipulating information to a positional instruction value based on the automatic operating information. The adder 131a sends the corrected positional instruction value to the subtractor 131b.

The subtractor 131b subtracts a present positional value detected by the rotation sensor E from the corrected positional instruction value to generate an angular deviation. The subtractor 131b sends the generated angular deviation to the position controller 131c.

The position controller 131c generates a speed instruction value based on the angular deviation sent from the subtractor 131b by arithmetic processing based on a transfer function and a proportional coefficient which are defined beforehand. The position controller 131c sends the generated speed instruction value to the subtractor 131e.

The differentiator 131d differentiates the present positional value information detected by the rotation sensor E to generate an amount of change in the rotation angle of the drive motor M per unit time, i.e., a present speed value. The differentiator 131d sends the generated present speed value to the subtractor 131e.

The subtractor 131e subtracts the present speed value sent from the differentiator 131d from the speed instruction value sent from the position controller 131c to generate a speed deviation. The subtractor 131e sends the generated speed deviation to the speed controller 131f.

The speed controller 131f generates a torque instruction value (current instruction value) based on the speed deviation sent from the subtractor 131e by arithmetic processing based on a transfer function and a proportional coefficient which are defined beforehand. The speed controller 131f sends the generated torque instruction value to the subtractor 131g.

The subtractor 131g subtracts the present current value detected by the current sensor C from the torque instruction value sent from the speed controller 131f to generate a current deviation. The subtractor 131g sends the generated current deviation to the drive motor M to drive the drive motor M.

Thus, the motion controller 131 controls the drive motor M to control the slave arm 101 so that the slave arm 101 performs the operation corrected from the operation related to the automatic operating information. Note that, when the operating mode of the slave arm 101 is the automatic mode, the positional instruction value based on the automatic operating information is sent to the subtractor 31b, and when the operating mode of the slave arm 101 is the manual mode, the positional instruction value based on the manipulating information is sent to the subtractor 131b.

The storage device 106 is configured, when the slave arm 101 performs the corrected operation, to automatically store the corrected operating information for causing the slave arm 101 to perform the corrected operation. Note that the storage device 106 may be configured to be selectable of whether the corrected operating information is to be stored, when the slave arm 101 performs the corrected operation. In this case, for example, the control device 103 may be configured to inquire whether the corrected operation is to be stored in the input device 107 after the corrected operation of the slave arm 101 is finished.

The motion controller 131 is capable of controlling the operation of the slave arm 101 by using the corrected operating information stored in the storage device 106 in subsequent operations. In this embodiment, the motion controller 131 is configured to control the operation of the slave arm 101 by using the latest corrected operating information stored in the storage device 106.

Figure 5:
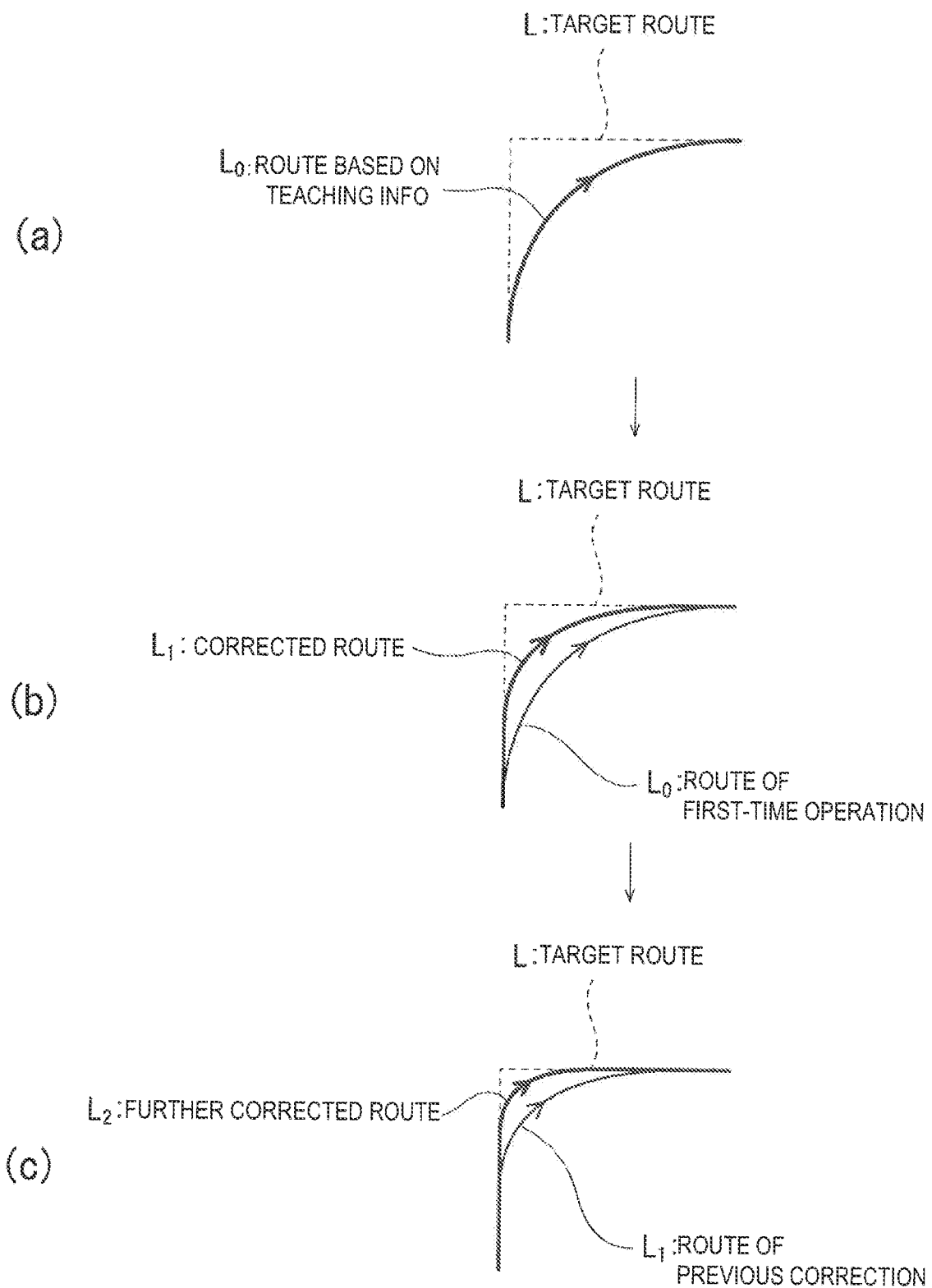
FIG. 5 is a view illustrating one example of correction of robot operation by the robot system of FIG. 2.

Below, with reference to FIGS. 5(a) to (c), the operational correction of the slave arm 101 by the robot system 100 is described with concrete examples. FIGS. 5(a) to (c) illustrate that, when the operating mode in which the slave arm 101 is operated is the correctable automatic mode, a route of the slave arm 101 (i.e., a route of the end effector) is corrected to a target route L each time the slave arm 101 is operated. In FIGS. 5(a) to (c), the target route L having a right-angled corner is illustrated by dashed lines.

In FIG. 5(a), a route $L_0$ of the slave arm 101 when the slave arm 101 is operated using the automatic operating information (teaching information) without the manipulation of the master arm 102 is illustrated by a thick line. From FIG. 1, it can be seen that the actual route $L_0$ is deviated partially from the target route L (especially, at the corner of the route L).

In FIG. 5(b), a route $L_1$ of the slave arm 101 when the master arm 102 is manipulated so that an amount of deviation with respect to the target route L becomes smaller than the route $L_0$ at the time of the first-time operation (the route of FIG. 5(a)) is illustrated by a thick line. Note that, in FIG. 5(b), the route $L_0$ in the first-time operation is illustrated by a thin line for reference.

The operator manipulates the master arm 102 so that the amount of deviation with respect to the target route L becomes smaller than the route $L_0$ at the time of the first-time operation to correct the operation of the slave arm 101 to the route $L_1$ corrected from the route $L_0$. Specifically, the motion controller 131 operates the slave arm 101 by using the automatic operating information (teaching information) in a state where the correctable automatic mode is selected as the operating mode in which the slave arm 101 is operated. The operator manipulates the master arm 102 so that the route approaches the target route L from the first-time route $L_0$, while the slave arm 101 is operating by using the automatic operating information. Thus, the route is corrected from the route $L_0$ of the slave arm 101 to the route $L_1$ of the slave arm 101. Then, the corrected information containing the corrected operating information for causing the slave arm 101 to operate on the route $L_1$ is stored in the storage device 106. Here, the number of corrections is counted, and the number of corrections [1] is stored in the storage device 106 as the corrected information.

In this embodiment, the motion controller 131 is configured to control the operation of the slave arm 101 by using the latest corrected operating information stored in the storage device 106. Thus, if the master arm 102 is not manipulated in the next operation, the slave arm 101 operates on the route $L_1$.

In FIG. 5(c), a route $L_2$ of the slave arm 101 when manipulating the master arm 102 so that the amount of deviation with respect to the target route $L_0$ becomes smaller than the route $L_1$ at the time of the previous correction (the route of FIG. 5(b)) is illustrated by a thick line. Note that, in FIG. 5(c), the route $L_1$ in the previous correction is illustrated by a thin line for reference.

The operator manipulates the master arm 102 so that the amount of deviation with respect to the target route L becomes smaller than the route $L_1$ at the time of the previous correction to correct the operation of the slave arm 101 to the route $L_2$ which is further corrected from the route $L_1$. Specifically, the motion controller 131 operates the slave arm 101 using the corrected operating information for causing the slave arm 101 to operate on the route $L_1$ as the automatic operating information in the state where the correctable automatic mode is selected as the operating mode in which the slave arm 101 is operated. The operator manipulates the master arm 102 so that the route approaches the target route L from the previous route $L_1$, while the slave arm 101 is operating by using the automatic operating information. Thus, the route is corrected from the route $L_1$ of the slave arm 101 to the route $L_2$ of the slave arm 101. Then, the corrected information containing the corrected operating information for causing the slave arm 101 to operate on the route $L_2$ is stored in the storage device 106. Here, the number of corrections is counted, and the number of corrections [2] is stored in the storage device 106 as the corrected information.

Thus, the route of the slave arm 101 is corrected so as to approach the target route L each time the slave arm 101 is operated. When the route of the slave arm 101 is corrected to the target route L and no more correction is necessary, the operator selects the automatic mode as the operating mode in which the slave arm 101 is operated by the mode selector 171 to operate the slave arm 101 completely automatically.

As described above, in this embodiment, the motion controller 131 stores in the storage device 106 the corrected information containing the corrected operating information for causing the slave arm 101 to perform the corrected operation, when the slave arm 101 performs the corrected operation. Thus, in one factory 10, each robot system 100 of the plurality of robot systems 100 is capable of sharing the corrected information stored in the storage device 106, and operating the robots based on the sharing corrected information. Also in other factories 10, by performing similar processing, the corrected information can be shared between the respective robot systems of the plurality of robot systems 100, and the robots can be operated based on the sharing corrected information. Therefore, the burdens of the correction in other robot systems 100 and the setup of a new robot system 100 are reduced.

[Processing of Server]

Figure 6:
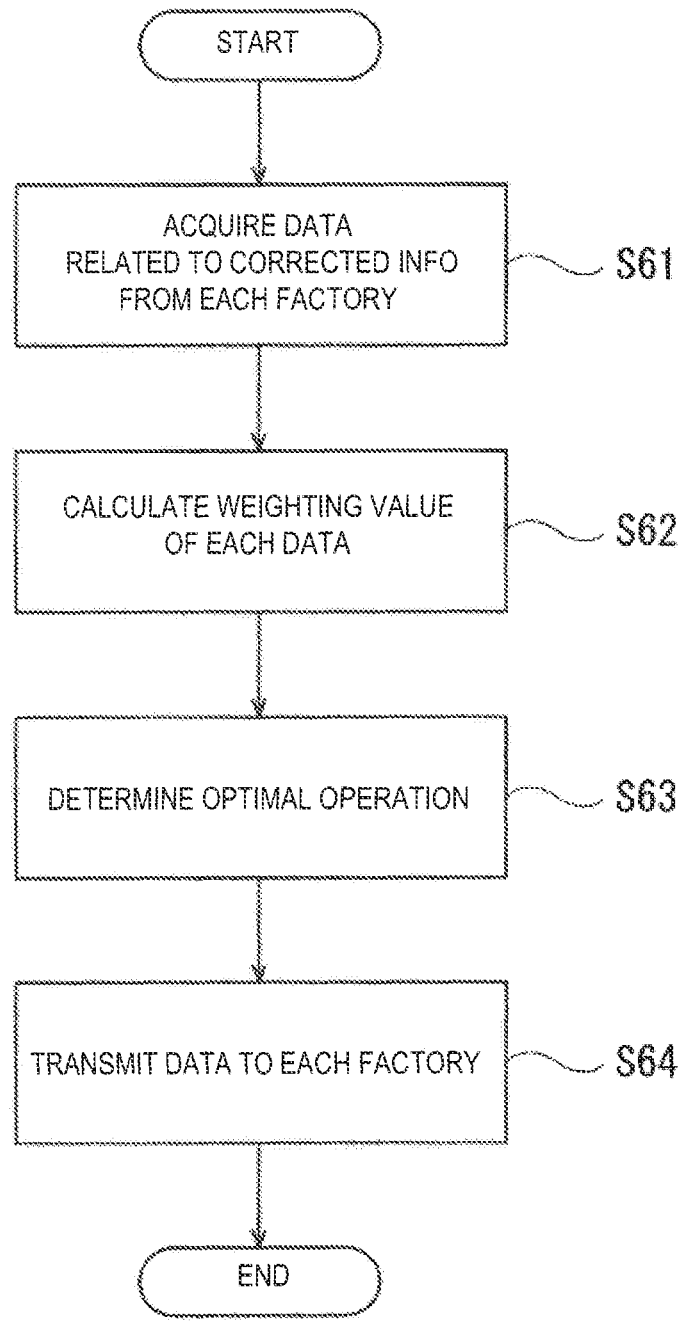
FIG. 6 is a flowchart illustrating one example of processing in a server of FIG. 1.

Moreover, the corrected information which is shared between the plurality of robot systems 100 is transmitted from each factory 10 (router) to the server 2 through the Internet 3 (see FIG. 1). Next, a procedure of information sharing processing which is executed by the server 2 is described using a flowchart of FIG. 6.

First, the server 2 receives data related to the corrected information on the plurality of robot systems 100 from each factory 10 (router) (Step S61). The data transmission to the server 2 from each factory 10 is performed, for example, at a certain interval. Here, the data related to the corrected information contains data for every number of corrections related to the corrected route of the slave arm 101.

Figure 7:
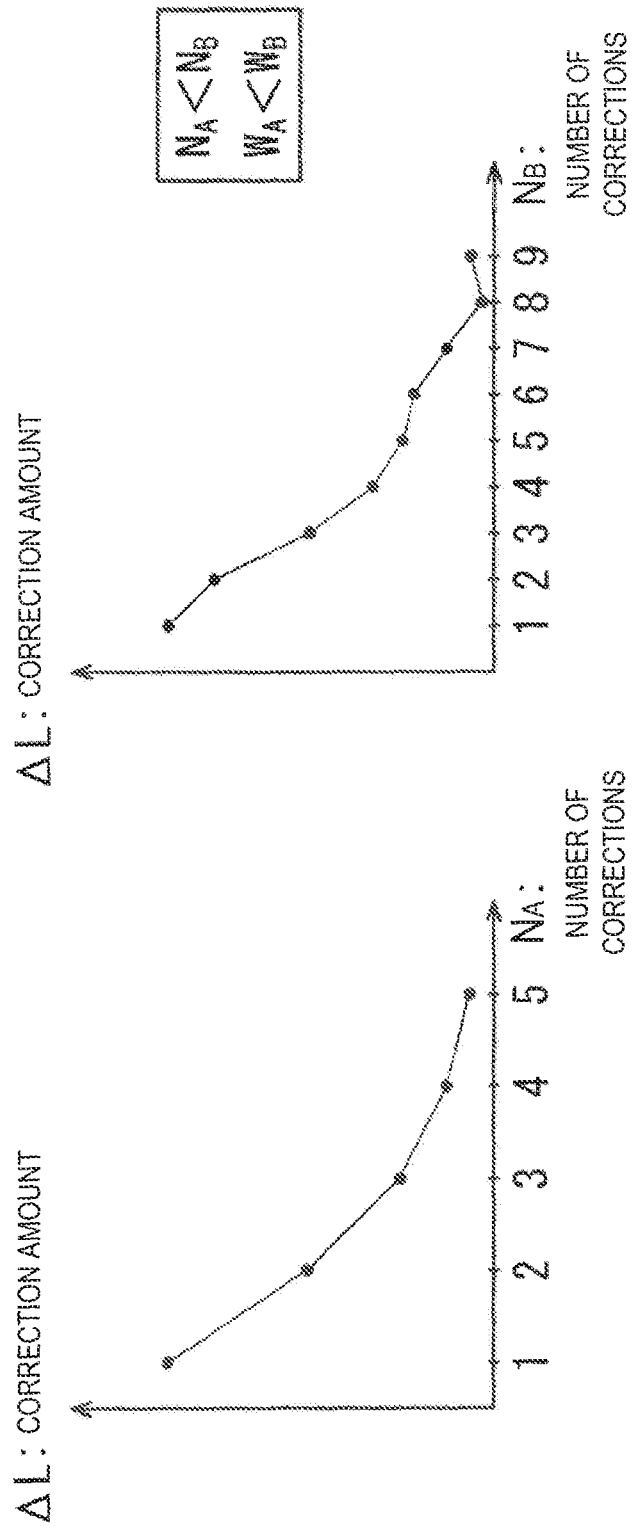
FIG. 7 illustrates graphs of one example of corrected information received by the server of FIG. 1.

Next, the server 2 calculates a weighting value according to the number of corrections based on the corrected operating information contained in the corrected information acquired from each factory 10 (Step S62). FIG. 7 illustrates graphs of one example of the corrected information received by the server 2. The left graph illustrates the corrected information received from the factory A, and the right graph illustrates the corrected information received from the factory B. The vertical axis of the graph indicates a correction amount ΔL of the robot operation, and the horizontal axis of the graph indicates the number of corrections N. Here, the correction amount ΔL is a difference between the previous value of the corrected operating information and the present value.

In the factories A and B, a case where a skilled person of the same level performs the correction is assumed. Thus, as illustrated in FIG. 7, in both graphs, although a first-time correction amount ΔL is larger, a second-time correction amount ΔL is smaller. Although the correction amount ΔL is about the same in the factories A and B, the factory B is greater in the number of corrections N than the factory A. Thus, the server 2 calculates the weighting values so that a weight $W_B$ of the factory B becomes larger than the weight $W_A$ of the factory A.

FIG. 8 illustrates one example of data managed by the server 2. As illustrated in FIG. 8, the server 2 manages for every factory, the latest corrected operating information and the number of corrections, and the weighting value according thereto. As illustrated in FIG. 8, the operational corrections of the robot have been made 50 times, in the factory A, and similar corrections have been made 1,000 times in the factory B, and similar corrections have been made 500 times in the factory E. In this embodiment, if the number of corrections is greater than a first given number of times (e.g., 700 times), it is determined that the reliability of the received data is high, and the weighting value is set to a larger value (e.g., 0.7) than a given reference value (e.g., 0.3), while if the number of corrections is less than a second given number of times (e.g., 100 times), it is determined that the reliability of the received data is low, and the weighting value is set to a smaller value (e.g., 0.1) than the given reference value (e.g., 0.3). Thus, the weighting value of the factory A is set to 0.1, the weighting value of the factory B is set to 0.7, and the weighting value of the factory E is set to 0.3. Here, each weighting value is standardized so that a sum total value thereof becomes 1.0. Note that the weighting value may be a value according to the number of corrections.

Next, the server 2 determines optimal operation of the robot (Step S63). In this embodiment, the server 2 calculates optimal operation $L_{OPT}$ of the robot by adding the weighting value according to the number of corrections to the corrected operating information of each of the plurality of robot systems 100 acquired from the plurality of factories 10, by using Formula (1).

$$L_{OPT} = L_A \times W_A + L_B \times W_B + \ldots + L_E \times W_E \qquad (1)$$

Here, $L_{OPT}$ represents optimal operating information, $L_A$ represents the latest corrected operating information of the factory A, and $W_A$ represents a weighting value corresponding to the number of corrections in the factory A. $L_B$ represents the latest corrected operating information of the factory B, $W_B$ represents a weighting value corresponding to the number of corrections in the factory B. $L_E$ represents the latest corrected operating information of the factory E, and $W_E$ represents a weighting value corresponding to the number of corrections in the factory E. Thus, since the weighting values are added to the data of the corrected operating information according to the number of corrections, the reliability of sample data improves.

At last, the server 2 transmits the data containing the optimal operating information $L_{OPT}$ determined at Step S63 to each factory 10 (Step S64). Note that it may be a data distribution technique in which the server 2 which provides the information transmits data to non-plural factory 10 (router) all at once, or a server-client technique in which each factory 10 (router) which is a client accesses to the server 2 which provides the information. Thus, the optimal operating information $L_{OPT}$ of the robot can be shared between the plurality of factories 10. Therefore, the burdens of the correction of the robot systems and the setup of a new robot system at the time of a factory construction are reduced.

According to this embodiment, for example, only by one skilled person correcting the operation of one robot system 100 of one factory 10, contents of the correction are reflected in all the robot systems 100 in the factory 10. Further, the optimal correction operation is determined by the server 2, and all the factories 10 can share the information.

As described above, in the robot system 100 according to this embodiment, the operation of the slave arm 101 during operation is correctable on real time by the master arm 102 which functions as the operation correcting device. Thus, the partial operational correction of the slave arm 101 can easily be made. Moreover, since the corrected operating information for performing the corrected operation is stored in the storage device 106, it is not necessary to correct by performing the same operation each time using the master arm 102, and the slave arm 101 is capable of automatically performing the corrected operation. Therefore, the operation taught to the slave arm 101 is easily correctable.

Moreover, in this embodiment, since the motion controller 131 controls the operation of the slave arm 101 by using the latest corrected operating information stored in the storage device 106, the operation can be gradually brought closer to the target operation each time the correction of the slave arm 101 using the master arm 102 is repeated.

The motion controller 131 does not need to use the latest corrected operating information stored in the storage device 106. For example, the operating information selector 172 may select one corrected operating information from a plurality of corrected operating information stored in the storage device 106. In this case, the same corrected operating information may be used every time until the corrected operating information is selected by the operating information selector 172. According to this configuration, even if the latest corrected operating information stored in the storage device 106 is not the optimal as information for causing the slave arm 101 to operate, the operating information selector 172 uses the corrected operating information when the correction is made appropriately.

Moreover, as illustrated in FIG. 3, the motion controller 131 may be configured to use the plurality of corrected operating information stored in the storage device 106 to generate new corrected operating information. The method of generating new corrected operating information is not limited in particular, but an algorithm suitable for bringing the operation closer to the target operation may be adopted. For example, it may be configured so that the corrected operating information for performing operation which is an average of the operations related to the plurality of stored corrected operating information is generated. Moreover, when generating the new corrected operating information, the corrected operating information on the past which has been used in order to generate the new corrected operating information may be deleted.

Moreover, in the embodiment described above, although the master arm 102 which is controllable of the route of the end effector of the slave arm 101 is described as the operation correcting device of the present disclosure, it may be, for example, a route operating device of another configuration, such as a joystick.

Second Embodiment

Below, a second embodiment is described. The fundamental configuration of an information sharing system 1 of this embodiment is similar to that of the first embodiment. Below, description of common configurations to the first embodiment is omitted, and only different configurations will be described.

In this embodiment, as compared with the first embodiment, it differs in that the server 2 adds to the corrected operating information a weighting value according to the latest correction amount of the correction amount $\Delta L$ which is a difference between the previous value of the corrected operating information and the present value.

Figure 9:
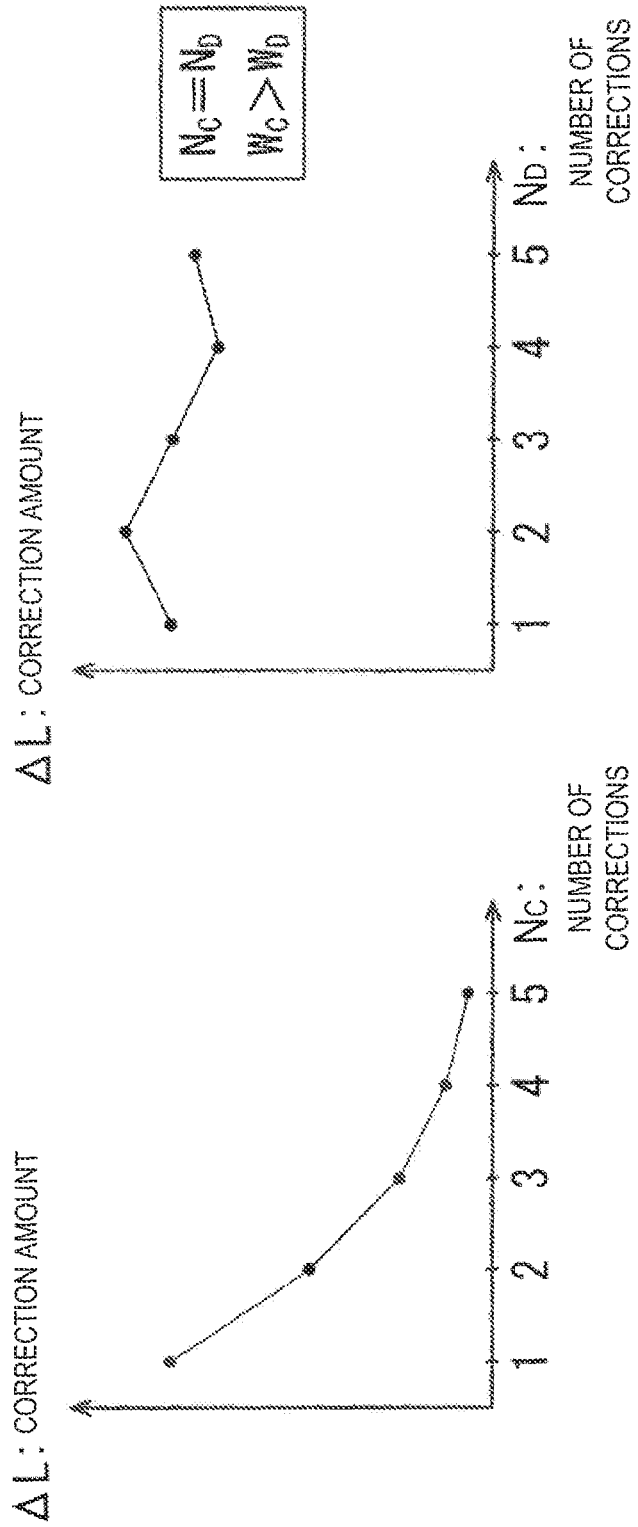
FIG. 9 illustrates graphs of one example of corrected information received by a server of an information sharing system according to a second embodiment.

FIG. 9 illustrates graphs of one example of the corrected information received by the server 2 of the information sharing system 1 according to the second embodiment. The left graph illustrates corrected information received from the factory C, and the right graph illustrates corrected information received from the factory D. The vertical axis of the graph indicates a correction amount $\Delta L$ of the robot operation and the horizontal axis of the graph illustrates the number of corrections N. It is assumed a case where the skilled person performs the correction in the factories C and C, and an unskilled person performs the correction in the factory D. As illustrated in FIG. 9, the number of corrections N is about the same in the factory C (left graph) and the factory D (right graph). Moreover, in the factory C, since the skilled person made the correction, although a first-time correction amount $\Delta L$ is larger, a second-time correction amount $\Delta L$ is smaller. On the other hand, in the factory D, since the unskilled person made the correction, the correction amount $\Delta L$ does not become smaller even after the first time and the second time. As a result, the latest correction amount $\Delta L$ becomes smaller in the factory C than the factory D. The latest correction amount becoming smaller means that the correction is mostly completed. Thus, the server 2 calculates weighting values so that a weight $W_C$ of the factory C is larger than a weight $W_D$ of the factory D. For example, the weighting value may be set to a larger value than a given reference value when the latest correction amount $\Delta L$ is small, and the weighting value is set to a smaller value than the given reference value when the latest correction amount $\Delta L$ is large.

According to this embodiment, since the weighting value according to the latest correction amount is added to the corrected operating information of each of the plurality of robot systems acquired from the plurality of factories 10, the reliability of sample data further improves. Thus, the optimal operation of the robot can be determined and all the factories 10 can share the information.

Third Embodiment

Below, a third embodiment is described. The fundamental configuration of an information sharing system 1 of this embodiment is similar to that of the first embodiment.

Below, description of the common configurations to the first embodiment is omitted, and only different configurations will be described.

Figure 10:
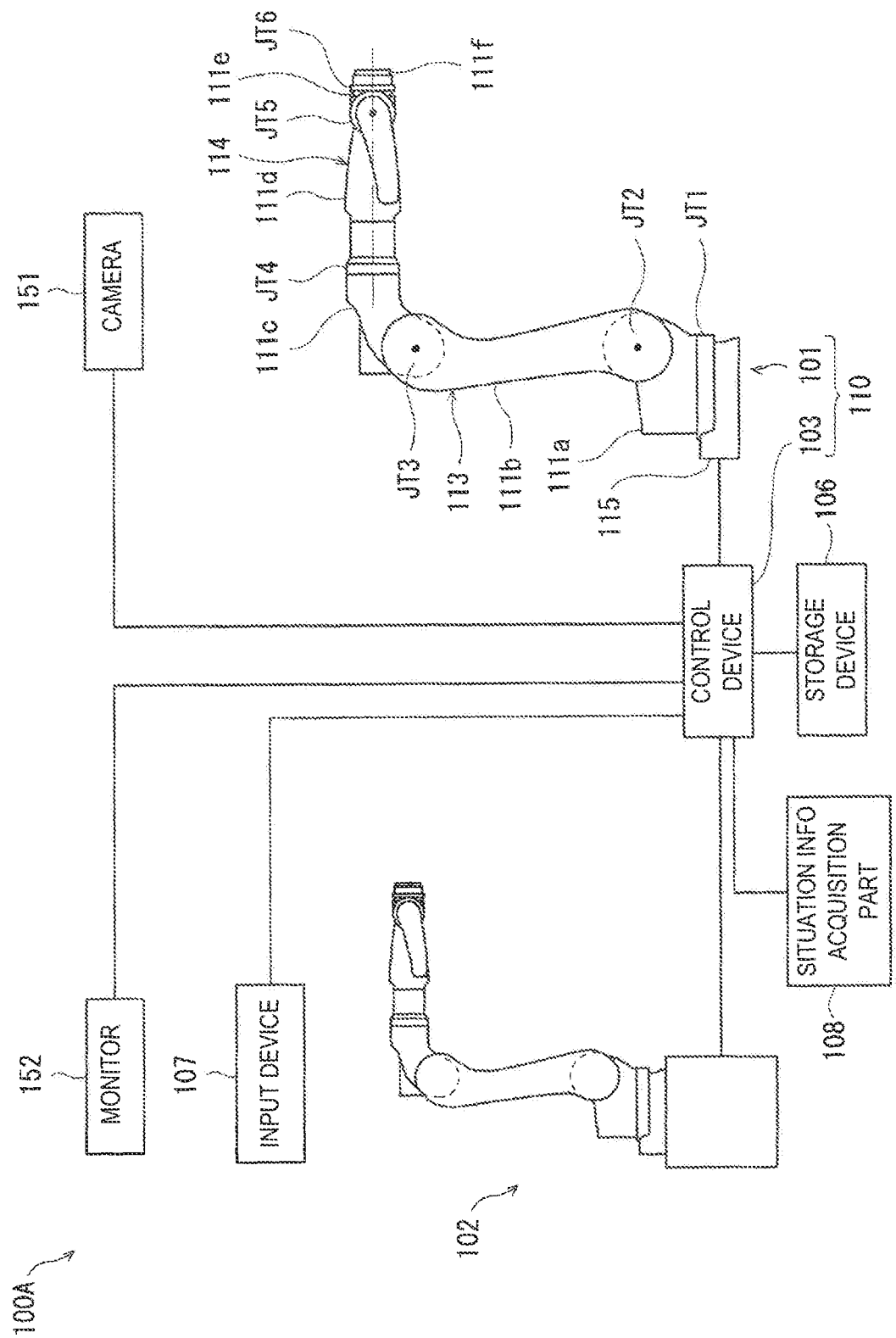
FIG. 10 is a schematic diagram illustrating a configuration of a robot system provided to an information sharing system according to a third embodiment.

FIG. 10 is a schematic diagram illustrating a configuration of a robot system provided to the information sharing system according to the third embodiment. As illustrated in FIG. 10, as compared with the first embodiment, it differs in that a robot system 100A is further provided with a situation information acquisition part 108 which acquires situation information indicative of a situation of each of the plurality of factories 10.

Meanwhile, a work environment influences the operations of the robots. For example, the work environment, such as climate, is different between a case where the robots are operated in the factory A in the U.S. and a case where the robots are operated in the factories B to E of other countries, such as Russia and China. Thus, the influences on the operations of the robots also differ. In this embodiment, the situation information is information which is used in order to recognize a situation around the slave arm 101 in the robot system 100A. Here, it may include information related to the temperature of the work area. That is, the situation information acquisition part 108 is a temperature sensor installed in the work area of each factory 10. Although the situation information acquisition part 108 is configured to transmit the acquired situation information to the control device 103, the situation information acquisition part 108 may also be configured to be provided with a network communication function, and to directly transmit the situation information to the server 2 through the Internet 3.

In this embodiment, the server 2 acquires temperature information on the work area as the situation information, as well as the corrected information of the plurality of robot systems 100A from each of the plurality of factories 10, and adds to the corrected operating information contained in the acquired corrected information, a weighting value according to the situation information.

Figure 11:
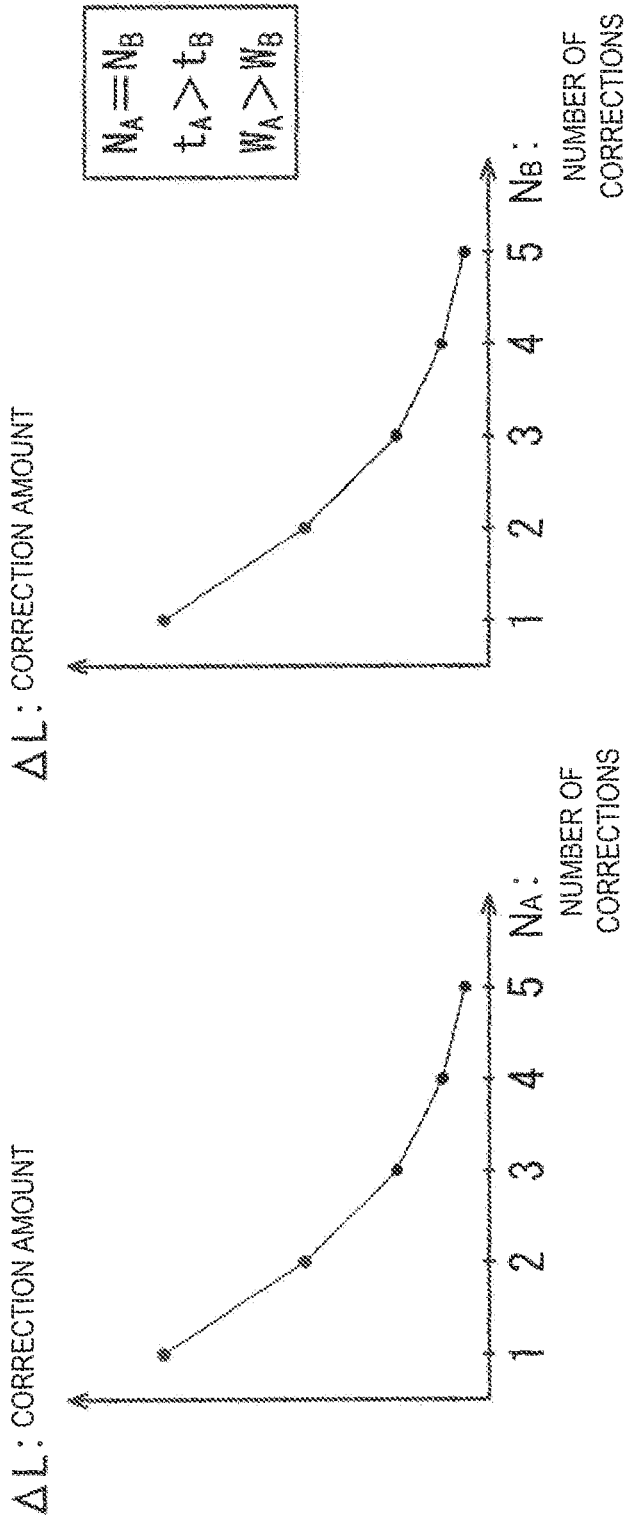
FIG. 11 illustrates graphs of one example of corrected information received by a server of the information sharing system.

FIG. 11 illustrates graphs of one example of the corrected information received by the server 2. The left graph illustrates the corrected information received from the factory A, and the right graph illustrates the corrected information received from the factory B. The vertical axis of the graph indicates a correction amount ΔL of the robot operation, and the horizontal axis of the graph indicates the number of corrections N. The number of corrections is about the same in the factory A (left graph) and the factory B (right graph). It is assumed that the skilled persons of the same level perform the correction in the factories A and B. Thus, the latest correction amount ΔL is also about the same in the factories A and B. However, the factory A is located in the U.S. where the climate is comparatively warm, and the factory B is located in Russia which is a cold region. Thus, a temperature $t_A$ of the work area of the factory A is higher than a temperature $t_B$ of the work area of the factory B. Therefore, the server 2 calculates the weighting values so that the weight $W_A$ of the factory A becomes larger than the weight $W_B$ of the factory B.

According to this embodiment, since the weighting value according to the situation information of each factory 10 is added to the acquired corrected operating information, the optimal operation of the robot can be determined for each of the plurality of factories 10, and all the factories 10 can share the information. Thus, the difference of the work environment between the factories 10 is absorbed, and the burdens of the correction of the robot system 100 in each factory 10 and the setup of the new robot system at the time of the factory construction are reduced. Moreover, when transmitting the operating information to each factory 10 from the server 2, the weighting value may be added to the shared information according to the work environment for each factory 10.

Note that, in this embodiment, although the information related to the temperature of the work area is illustrated as the information which is used in order to recognize the situation around the slave arm 101, the situation information may be the humidity of the work area, or a time window or season when the slave arm 101 is operated. For example, if the slave arm 101 is a sealing robot which applies seal adhesive with viscosity, the viscous resistance of the seal adhesive may vary with the time of working. In such a case, the operational correction of the slave arm 101 can be made easier by using the automatic operating information suitable for the viscous resistance of the seal adhesive.

Note that, although each of the robot systems 100A is configured to be provided with the situation information acquisition part 108 in this embodiment, the situation information acquisition part 108 may be installed in each factory 10.

Other Embodiments

Note that, in the embodiments described above, although the corrected information is stored in the storage device 106 of the robot system 100, it may be stored in other computers connected with the LAN 3, or may be stored in the server 2 connected with the Internet 3.

It is apparent for a person skilled in the art that many improvements and other embodiments of the present disclosure are possible from the above description. Therefore, the above description is to be interpreted only as illustration, and it is provided in order to teach a person skilled in the art the best mode which implements the present disclosure. Details of one or both of the structures and the functions of the present disclosure may be substantially changed without departing from the spirit of the present disclosure.

INDUSTRIAL APPLICABILITY

The present disclosure is useful at the manufacturing sites where many industrial robots are introduced.

DESCRIPTION OF REFERENCE CHARACTERS

1 Information Sharing System
2 Server
3 Internet (Network)
4 LAN (Network)
10 Factory
40 LAN Cable
100, 100A Robot System
101 Slave Arm (Robot Main Body)
102 Master Arm (Operation Correcting Device)
103 Control Device
106 Storage Device
107 Input Device
108 Situation Information Acquisition Part
131 Motion Controller
151 Camera
152 Monitor

What is claimed is:
1. An information sharing system between a plurality of robot systems, the information sharing system comprising:
a plurality of robot systems connected to and configured to communicate with each other through a network, the plurality of robot systems being configured to preset a given operation of a robot arm and repeat a correction of the given operation; and a storage device connected with the network and configured to store corrected operating information causing the robot arm to execute the given operation corrected in at least one robot system of the plurality of robot systems, the at least one robot system of the robot systems includes (i) a camera configured to capture an image of a work situation of the robot arm, and (ii) a monitor displaying the captured image for an operator to view the work situation of the robot arm, and the at least one robot system of the robot systems is configured to correct a route of the robot arm in real time by input from the operator while the operator is viewing the monitor when the robot arm is automatically operating and performing an operation on a work object, wherein each robot system of the plurality of robot systems shares the corrected operating information stored in the storage device and operates the robot arm based on the shared corrected operating information.

2. The information sharing system of claim 1, wherein:
the plurality of robot systems are respectively installed in each of a plurality of factories, and
the information sharing system further comprises a server connected to the storage device and the plurality of robots through the network, the server being configured to:
  acquire the corrected operating information of each the plurality of robot systems from each of the plurality of factories, and
  add weighting values according to the number of corrections to the corrected operating information in order to determine an optimal operation for the given operation of the robot arm.

3. The information sharing system of claim 1, wherein:
the plurality of robot systems are respectively installed in each of a plurality of factories, and
the information sharing system further comprises a server connected to the storage device and the plurality of robots through the network, the server being configured to:
  acquire the corrected operating information of each of the plurality of robot systems from each of the plurality of factories, and
  add weighting values to the corrected operating information contained in the acquired corrected information to determine an optimal operation for the given operation of the robot arm, the weighting values being based on a latest correction amount among correction amounts that are differences between a previous value and a present value of the corrected operating information.

4. The information sharing system of claim 1, wherein:
the plurality of robot systems are installed in each of a plurality of factories where work environments differ from each other,
the information sharing system further comprises a sensor configured to acquire situation information indicating a situation of each of the plurality of factories,
the information sharing system further comprises a server connected to the storage device and the plurality of robots through the network, and
the server acquires the corrected operating information and the situation information of the plurality of robot systems from each of the plurality of factories, and adds weighting values according to the situation information to the corrected operating information in order to determine an optimal operation for the given operation of the robot arm for each of the plurality of factories.

5. The information sharing system of claim 1, wherein a robot main body is a slave arm, and an operation correcting device is a master arm installed outside a work area of the slave arm.

6. A method of sharing information between a plurality of robot systems, the plurality of robot systems being connected to and configured to communicate with each other through a network, the plurality of robot systems being configured to preset a given operation of a robot arm and repeat a correction of the operation, the method comprising:
storing, in a storage device connected with the network, corrected operating information causing the robot arm to execute the given operation corrected in at least one robot system of the plurality of robot systems, the at least one robot system of the robot systems includes (i) a camera configured to capture an image of a work situation of the robot arm, and (ii) a monitor displaying the captured image for an operator to view the work situation of the robot arm, and the at least one robot system of the robot systems is configured to correct a route of the robot arm in real time by input, from the operator while the operator is viewing the monitor when the robot arm is automatically operating and performing an operation on a work object;
sharing the corrected operating information stored in the storage device, in each of the plurality of robot systems; and
operating the robot arm based on the shared corrected operating information.

* * * * *